(12) United States Patent
Gulani et al.

(10) Patent No.: US 10,147,314 B2
(45) Date of Patent: Dec. 4, 2018

(54) MAGNETIC RESONANCE IMAGING (MRI) BASED QUANTITATIVE KIDNEY PERFUSION ANALYSIS

(71) Applicant: Case Western Reserve University, Cleveland, OH (US)

(72) Inventors: Vikas Gulani, Cleveland Heights, OH (US); Katherine Wright, Cleveland Heights, OH (US); Nicole Seiberlich, Shaker Heights, OH (US); Mark Griswold, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 878 days.

(21) Appl. No.: 14/084,678

(22) Filed: Nov. 20, 2013

(65) Prior Publication Data
US 2014/0294734 A1    Oct. 2, 2014

Related U.S. Application Data

(60) Provisional application No. 61/806,907, filed on Mar. 31, 2013.

(51) Int. Cl.
*A61K 49/06*  (2006.01)
*G01R 33/56* (2006.01)
(Continued)

(52) U.S. Cl.
CPC ............ *G08C 23/06* (2013.01); *A61B 5/0017* (2013.01); *A61B 5/0073* (2013.01);
(Continued)

(58) Field of Classification Search
CPC ..... A61B 5/0017; A61B 5/0073; A61B 5/055; A61B 5/4244; A61K 49/06;
(Continued)

(56) References Cited

U.S. PATENT DOCUMENTS 5,590,654 A  *  1/1997  Prince .......................... 600/420
6,841,998 B1 *  1/2005  Griswold ...................... 324/309
(Continued)

*Primary Examiner* — Michael Rozanski
(74) *Attorney, Agent, or Firm* — Quarles & Brady LLP

(57) ABSTRACT

Example apparatus and methods provide improved spatial and temporal resolution over conventional magnetic resonance renography (MRR). Example apparatus and methods reconstruct under-sampled three-dimensional (3D) data associated with nuclear magnetic resonance (NMR) signals acquired from a kidney. The data is reconstructed using a 3D through-time non-Cartesian generalized auto-calibrating partially parallel acquisitions (GRAPPA) approach. Example apparatus and methods produce a quantized value for a contrast agent concentration in the kidney from a signal intensity in the data based, at least in part, on a two compartment model of the kidney. The two compartment model includes a plasma compartment and a tubular compartment. The quantized value describes a perfusion parameter for the kidney or a filtration parameter for the kidney. Greater precision is achieved for estimates of the perfusion parameter or filtration parameter as a result of the quantization performed on data acquired with greater spatial resolution and temporal resolution.

28 Claims, 9 Drawing Sheets

(51) Int. Cl.
*G08C 23/06* (2006.01)
*G01R 33/36* (2006.01)
*G01R 33/48* (2006.01)
*G01R 33/58* (2006.01)
*A61B 5/00* (2006.01)
*G01R 33/563* (2006.01)
*A61B 5/055* (2006.01)

(52) U.S. Cl.
CPC ............ *A61B 5/4244* (2013.01); *A61K 49/06* (2013.01); *G01R 33/3614* (2013.01); *G01R 33/3692* (2013.01); *G01R 33/4822* (2013.01); *G01R 33/56* (2013.01); *G01R 33/5608* (2013.01); *G01R 33/56366* (2013.01); *G01R 33/58* (2013.01); *A61B 5/055* (2013.01)

(58) Field of Classification Search
CPC ............ G01R 33/3614; G01R 33/3692; G01R 33/4822; G01R 33/56; G01R 33/5608; G01R 33/56366; G01R 33/58; G08C 23/06; H05K 999/99
See application file for complete search history.

(56) References Cited

U.S. PATENT DOCUMENTS

| | | | |
|---|---|---|---|
| 7,283,862 B1* | 10/2007 | Slavin et al. ................. | 600/420 |
| 7,941,204 B1* | 5/2011 | Wang et al. ................. | 600/420 |
| 9,186,086 B2* | 11/2015 | Lorenz ................... | A61B 5/055 |
| 2005/0058598 A1* | 3/2005 | Degani et al. ............... | 424/1.11 |
| 2009/0324043 A1* | 12/2009 | Sun et al. ..................... | 382/131 |
| 2011/0044524 A1* | 2/2011 | Wang ..................... | G01R 33/54 |
| | | | 382/131 |
| 2011/0098556 A1* | 4/2011 | Blomqvist et al. .......... | 600/419 |
| 2013/0084246 A1* | 4/2013 | Moats et al. ................. | 600/410 |
| 2014/0015527 A1* | 1/2014 | Griswold et al. ............ | 324/309 |
| 2014/0039300 A1* | 2/2014 | Gjesdal et al. .............. | 600/420 |
| 2014/0062477 A1* | 3/2014 | Carroll et al. ............... | 324/309 |
| 2014/0154185 A1* | 6/2014 | Van Zijl et al. ............. | 600/411 |
| 2015/0327783 A1* | 11/2015 | Wang ................... | A61B 5/0263 |
| | | | 600/419 |

\* cited by examiner

MAGNETIC RESONANCE IMAGING (MRI) BASED QUANTITATIVE KIDNEY PERFUSION ANALYSIS

CROSS-REFERENCE TO RELATED APPLICATIONS

This application claims the benefit of U.S. Provisional Patent Application 61/806,907 titled "Medical Imaging" filed Mar. 31, 2013.

STATEMENT REGARDING FEDERALLY SPONSORED RESEARCH

This invention was made with government support under the grant(s) EB011527, HL094557, and RR000400 awarded by the National Institutes of Health. The government has certain rights in the invention.

BACKGROUND

The primary functions of the kidneys are to filter and excrete metabolic waste products. The kidneys help maintain homeostasis by regulating acid-base balance, blood pressure, and fluid volume. Renal function is assessed to determine renal sufficiency, renovascular disease, metabolic disorders, and other conditions. Assessment of renal perfusion is helpful in analyzing several renal diseases, for analyzing renal artery stenosis (RAS), for analyzing renal transplant dysfunction (e.g., chronic ischemic nephropathy, drug nephropathy), and for other purposes.

Since the kidney has different regions, compartmental models have been used to study the kidney. A compartmental analysis is a form of deterministic analysis that divides a physiological system into a number of interconnected compartments. A compartment may be an anatomical, physiological, chemical, or physical subdivision of a system. A compartmental model may be characterized by number of compartments, number of inputs, or number of outputs. In a deterministic model, analytical expressions are used to describe behavior. This compares to a stochastic model where behavior is determined by random processes that are described by probability functions. Since the kidneys have a single blood supply, the kidney may be studied using a single input, dual compartment model. The kidney may be represented as a combination of at least two homogeneous compartments, a vascular component and a tubular component.

Magnetic resonance imaging (MRI) provides highly detailed anatomical information. Dynamic contrast-enhanced (DCE) MRI of the kidney monitors the transit of contrast materials (e.g., gadolinium (Gd) chelates) through the intrarenal regions, the renal cortex, the medulla, and the collecting system of the kidneys. MRI using DCE may experience several stages. For example, at a first time, a bolus of contrast agent may arrive in the large vessels of the kidney. Cortical enhancement may then occur between approximately 20 and 30 seconds after the contrast agent is administered. This cortical enhancement may reflect the contrast within the renal vasculature. Medullary enhancement may then occur approximately 60 seconds after cortical enhancement. The medullary enhancement may be dominated by contrast in renal tubules. Enhancement in the collecting system of the kidney may then occur starting around 180 seconds after medullary enhancement. By analyzing the enhancement at various time points after administration of contrast agent, clinically relevant parameters including renal blood flow (RBF), glomerular filtration rate (GFR), cortical blood volume, and medullary blood volume may be measured. However, acquiring sufficient signals to perform quantization that is sufficient to support meaningful functional analysis requires a combination of spatial resolution and temporal resolution that was not conventionally available.

Conventionally, different methods have been used to quantify renal perfusion using information acquired by MRI. These methods included the upslope method, semi-quantitative parametric methods, de-convolution methods, and various compartmental models. Unfortunately, the temporal resolution provided by conventional MRI systems may not have been sufficient to support functional examinations. Additionally, applying conventional under-sampling to improve temporal resolution may have negatively impacted spatial resolution to the point where functional examinations were difficult, if even possible at all, to achieve.

Quantitative evaluation of renal functions including perfusion and filtration is employed for diagnosing and monitoring vascular diseases, hypertension, obesity, diabetes, renal transplantation, urinary tract obstruction, and other processes. While conventional systems have provided some insights into these conditions and other conditions, conventional systems have been limited by imaging technology that could not provide dynamic acquisitions with adequate spatial resolution and temporal resolution to provide dynamic quantitative data from functional examinations.

Conventional studies have typically employed T1-weighted, gradient recalled echo (GRE) sequences. T1 refers to spin-lattice relaxation, T2 refers to spin-spin relaxation. Three-dimensional (3D) acquisitions may provide continuous whole-kidney coverage to assess whole-kidney function, but have been limited by longer acquisition times. 3D T1 mapping within one breath-hold has typically been challenging. Thus, two-dimensional (2D) images have typically been acquired with higher temporal and spatial resolution. However, the 2D image approach may have been limited to a single representative slice or selected slices, which precluded whole kidney functional analysis. Achieving higher temporal and spatial resolution facilitates achieving greater precision in estimating renal perfusion and filtration rates.

Kinetic modeling involves converting an MRI signal into a gadolinium (Gd) concentration. This conversion has been challenging because MR signal intensity varies with contrast agent concentration, pulse sequence parameters, pre-contrast relaxation times, blood flow velocity, and other factors. Additionally, the relationship between signal and concentration is non-linear. Conventional spatial and temporal resolution may have been insufficient to provide adequate signal for meaningful functional analysis involving kinetic modeling.

DETAILED DESCRIPTION

Figure 1A:
FIGS. 1A and 1B illustrate representative single partition images from a volume reconstructed using 3D through-time non-Cartesian generalized auto-calibrating partially parallel acquisitions (GRAPPA).

Example apparatus and methods perform highly under-sampled non-Cartesian acquisitions and three dimensional (3D) through-time non-Cartesian generalized auto-calibrating partially parallel acquisitions (GRAPPA) reconstructions to acquire 3D volumes of a kidney with improved spatial resolution and temporal resolution from which quantized data can be acquired with a desired precision. The quantized data supports analyzing renal parameters including perfusion and function (e.g., filtration). Example apparatus and methods perform quantitative dynamic contrast enhanced (DCE) MRI using non-Cartesian parallel imaging techniques with high degrees of under-sampling.

Experiments that included free-breathing renal DCE MRI were performed on asymptomatic volunteers following injection of Gd-DTPA on a 3T MRI apparatus. Gd refers to gadolinium. Gd-DTPA refers to a complex of gadolinium with a chelating agent, diethylenetriamine penta-acetic acid ($C_{28}H_{54}GdN_5O_{20}$, Molecular Weight: 937.99986). Other contrast agents may be employed. In one embodiment, data was acquired using a 3D stack-of-stars trajectory. Other data acquisitions may be employed. Data acquisition was accelerated by under-sampling partitions or volumes of a kidney radially by a factor of 8, which produced an acceleration factor of 12.6 with respect to the Nyquist criterion. Other under-sampling rates may be employed. The acceleration facilitated by the under-sampling yielded a temporal resolution of better than three seconds per frame, where a frame included data for a 3D volume. Temporal resolution of better than three seconds per frame is sufficient to support high precision functional examinations that provide quantitative data about renal perfusion or function (e.g., filtering) In different experiments with different volunteers, the scanning parameters were tailored to fit the anatomy of the volunteer while maintaining the scan time of less than three seconds per frame or volume.

In one example, a Fast Low Angle Shot (FLASH) MRI readout was employed with repetition time (TR) set to 3.4-3.68 ms, echo time (TE) set to 1.24-1.36 ms, and flip angle (FA) set to 18 degrees. Other TR, TE, and FA may be employed. In one example, a field of view (FOV) was set to 385-470 mm$^2$×87-108 mm and spatial resolution achieved was 2.41-2.81 mm$^3$. Other FOV may be employed. Spatial resolution of 2.41-2.81 mm$^3$ is sufficient to support high precision functional examinations that provide quantitative data about renal perfusion or function (e.g., filtration). In one example, the bandwidth was set between 580-820 Hz/pixel with 20-24 projections/partition. Other bandwidths and projections/partition may be employed. In one example, partial Fourier transformation in the partition direction was employed. Up to eighty volumes were acquired. Different numbers of volumes may be acquired in different embodiments. In one example, data associated with the up to eighty volumes was reconstructed using 3D through-time non-Cartesian (e.g., radial, spiral) GRAPPA. In one example, the data was then gridded using a non-uniform fast Fourier transform.

Acquiring the under-sampled data is just part of the procedure for producing quantized data concerning renal perfusion or function. The magnetic resonance (MR) signal data is quantized by converting signal intensity in the MR signal data to contrast agent concentration. In one example, to quantize results, signal intensity values may be converted to contrast agent concentration based, at least in part, on reference or calibration values provided from imaging of reference samples. The reference samples may be, for example, vials with known concentrations of the contrast agent. With quantized concentration values available, concentration time courses may be produced and then employed to estimate or illustrate perfusion parameters or filtration parameters. The parameters may be estimated using, for example, a non-linear least squares fit approach. The quantized concentration values may be produced or analyzed based, at least in part, on a compartment model of the kidney.

In one example, a single input two-compartment model may be used to obtain estimates of perfusion parameters based, at least in part, on the quantized contrast agent concentration. The two compartment model may include a plasma compartment and a tubular compartment. The perfusion parameters may include perfusion (Fp), mean transit time in a plasma compartment (Tp), tubular flow (Ft), and mean transit time in the tubular component (Tt). Other parameters may also be examined. While a single input two-compartment Model is described, in other examples different compartment models may be employed.

Producing quantized data about contrast agent concentration facilitates producing outputs that may not be available to conventional systems. In one embodiment, a pixel-wise parameter mapping may be performed. Pixel-wise parameter mapping of the renal cortex may produce a viewable parameter map that illustrates the renal perfusion or function. The pixel-wise parameter mapping may be segmented by thresholding signal intensity values in a frame during different enhancements. For example, the pixel-wise parameter mapping may be segmented during corticomedullary enhancement.

Figure 1B:

FIGS. 1A and 1B illustrate representative single partition images from a volume reconstructed using 3D through-time non-Cartesian GRAPPA. FIG. 1A shows a single slice at approximately 30 seconds after a contrast agent was introduced to a kidney and FIG. 1B shows the slice at approximately 132 seconds after the contrast agent was introduced. The series of two images shows the flow and concentration of the contrast agent over time. While two images are illustrated, a series of more than two images (e.g., one hundred images) acquired at better than three seconds per frame may be acquired and displayed.

Figure 2:
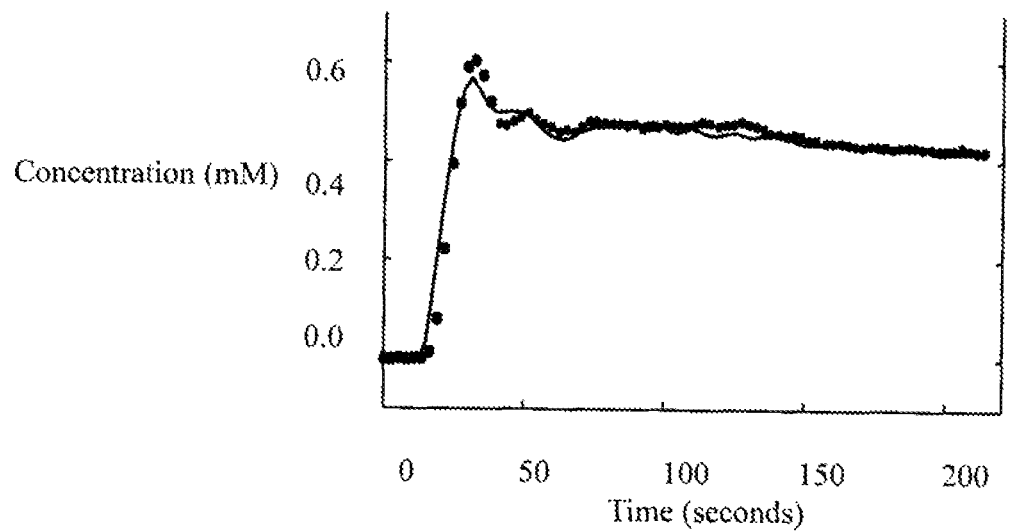
FIG. 2 illustrates a concentration time-course of data acquired from the renal parenchyma.

FIG. 2 illustrates a concentration time-course of data acquired from the renal parenchyma. The series of images acquired at better than three seconds per frame (e.g., 2 seconds/frame, 1.5 seconds/frame, 1 second/frame) provides data sufficient to produce the Illustrated concentration time course and other time courses with clinically relevant precision. Conventional systems that acquire fewer images and at lower quality may not be sufficient to produce time courses that are accurate enough to be clinically relevant (e.g., accurate enough to support a diagnosis).

Figures 3A, 3B:
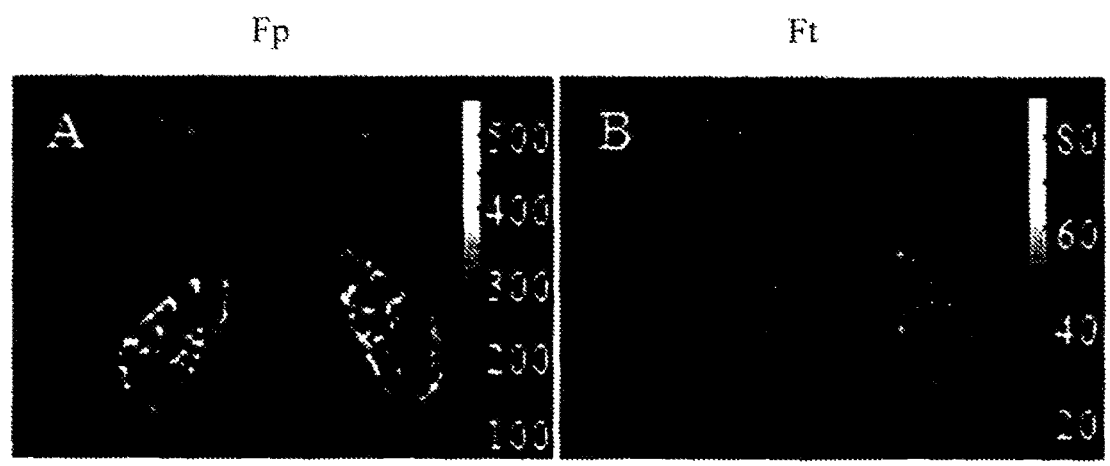
FIGS. 3A and 3B illustrate representative parameter maps of perfusion (Fp) and tubular flow (Ft).

FIGS. 3A and 3B illustrate representative parameter maps of perfusion (Fp) and tubular flow (Ft). Fp and Ft are measured in ml/min/100 ml tissue. The parameter maps are the result of a pixel-wise analysis. For example, FIG. 3A is the result of pixel-wise analysis of perfusion (Fp) data while FIG. 3B is the result of pixel-wise analysis of tubular flow (Ft) data. Acquiring frames at the improved temporal resolution (e.g., better than three seconds per frame) and at the improved spatial resolution (e.g., 2.4 mm$^3$, 800 Hz/pixel, 24 projections/partition) provides sufficient data to support the pixel-wise analysis that produces the representative parameter maps.

Some portions of the detailed descriptions that follow are presented in terms of algorithms and symbolic representations of operations on data bits within a memory. These algorithmic descriptions and representations are used by those skilled in the art to convey the substance of their work to others. An algorithm is considered to be a sequence of operations that produce a result. The operations may include creating and manipulating physical quantities that may take the form of electronic values. Creating or manipulating a physical quantity in the form of an electronic value produces a concrete, tangible, useful, real-world result.

It has proven convenient at times, principally for reasons of common usage, to refer to these signals as bits, values, elements, symbols, characters, terms, numbers, and other terms. It should be borne in mind, however, that these and similar terms are to be associated with the appropriate physical quantities and are merely convenient labels applied to these quantities. Unless specifically stated otherwise, it is appreciated that throughout the description, terms including processing, computing, and determining, refer to actions and processes of a computer system, logic, processor, or similar electronic device that manipulates and transforms data represented as physical quantities (e.g., electronic values).

Example methods may be better appreciated with reference to flow diagrams. For simplicity, the illustrated methodologies are shown and described as a series of blocks. However, the methodologies may not be limited by the order of the blocks because, in some embodiments, the blocks may occur in different orders than shown and described. Moreover, fewer than all the illustrated blocks may be required to implement an example methodology. Blocks may be combined or separated into multiple components. Furthermore, additional or alternative methodologies can employ additional, not illustrated blocks.

Figure 4:
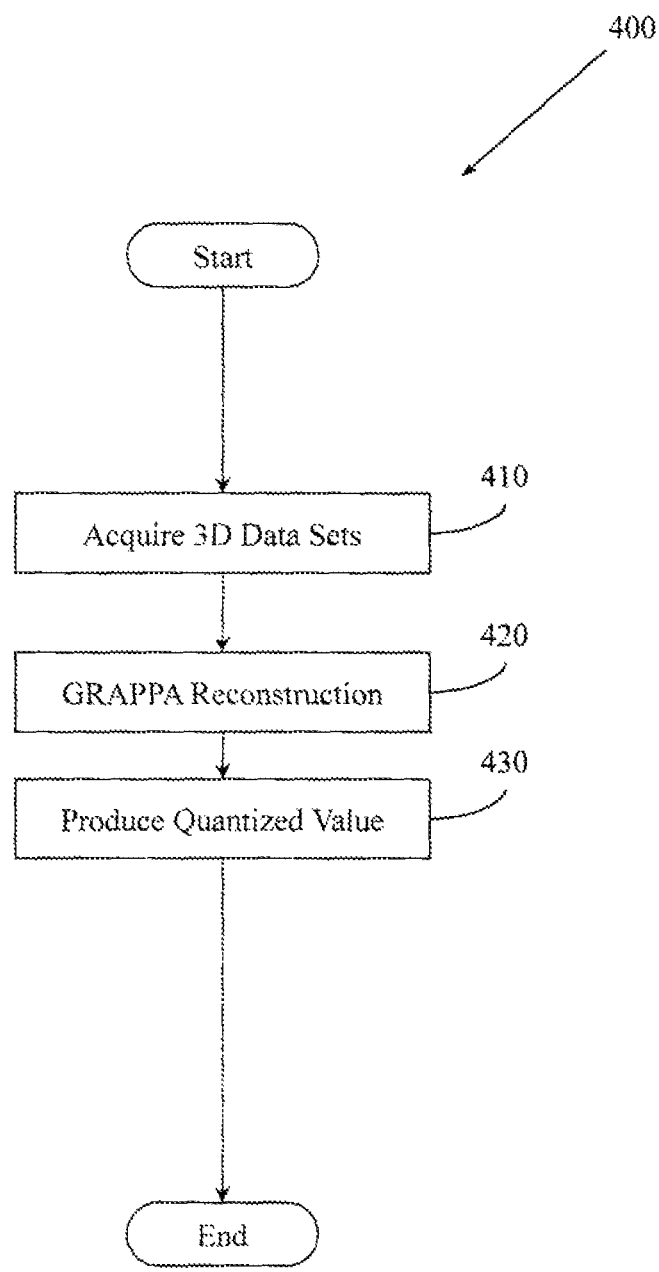
FIG. 4 illustrates an example method associated with MRI-based quantitative kidney perfusion analysis.

FIG. 4 illustrates an example method 400 associated with MRI-based quantitative kidney perfusion analysis. Method 400 includes, at 410, controlling an MRI apparatus to acquire a series of 3D data sets. Members of the series of 3D data sets are portions (e.g., partial volumes) of a kidney. In one embodiment, the series of 3D data sets are acquired during a DCE MRI procedure that includes presenting a contrast agent to the kidney. The contrast agent may be, for example, Gd-DTPA. The DCE MRI procedure may cause corticomedullary enhancement in the kidney, an intra-renal enhancement in the kidney, a renal cortex enhancement in the kidney, an enhancement in the collecting system of the kidney, or other enhancements.

In one embodiment, the MRI apparatus may be controlled to acquire the series of 3D data sets using a 3D stack-of-stars trajectory. To improve temporal resolution, the MRI apparatus may be controlled to acquire the series of 3D data sets using non-Cartesian under-sampling at a factor of at least eight. Since certain functional analyses may only be performed with clinically relevant precision if there is adequate temporal resolution, in one example, the MRI apparatus may be controlled to acquire the series of 3D data sets with a temporal resolution of better than 3 seconds per frame. Since certain functional analyses may only be performed with clinically relevant precision if there is adequate spatial resolution, example apparatus and methods improve temporal resolution without sacrificing spatial resolution. Therefore, method 400 may include controlling the MRI apparatus to acquire the series of 3D data sets with a spatial resolution of better than 2.85 mm$^3$ (e.g., 2.5 mm$^3$, 2.25 mm$^3$, 2.0 mm$^3$).

In one embodiment, the MRI apparatus may be controlled to acquire the series of 3D data sets using a range of 580-820 Hz/pixel or using a range of 20-24 projections/partition. In one embodiment, the MRI apparatus may be controlled to acquire the series of 3D data sets using a partial Fourier transformation in the partition direction.

Method 400 also includes, at 420, controlling the MRI apparatus to reconstruct the series of 3D data sets into a series of 3D images. In one embodiment, the images are reconstructed using a 3D through-time non-Cartesian GRAPPA approach. The series of 3D data sets may include, for example, 50 data sets, 75 data sets, 100 data sets, or more data sets. Since improved spatial resolution and temporal resolution are available when performing through-time 3D non-Cartesian GRAPPA, reconstructing the series of 3D data sets may be performed without view sharing.

Method 400 also includes, at 430, producing a quantified value for a renal perfusion parameter for the kidney. The quantified value is based, at least in part, on a member of the series of 3D images. The quantified value may concern, for example, perfusion, mean transit time in the plasma compartment, tubular flow, mean transit time in the tubular compartment, or other values. Producing the quantified value may include referencing or using a two compartment model of a kidney. In one embodiment, the two compartment model includes a plasma compartment and a tubular compartment.

Conventional systems may require four second temporal resolution to achieve just ten percent precision in estimating an analyzed parameter. Example systems have improved spatial and temporal resolution. Therefore, in different embodiments, method 400 may include producing the quantified value for the renal perfusion parameter with at least 10% precision, with at least 25% precision, with at least 50% precision, with at least 75% precision, or with other precisions.

Figure 5:
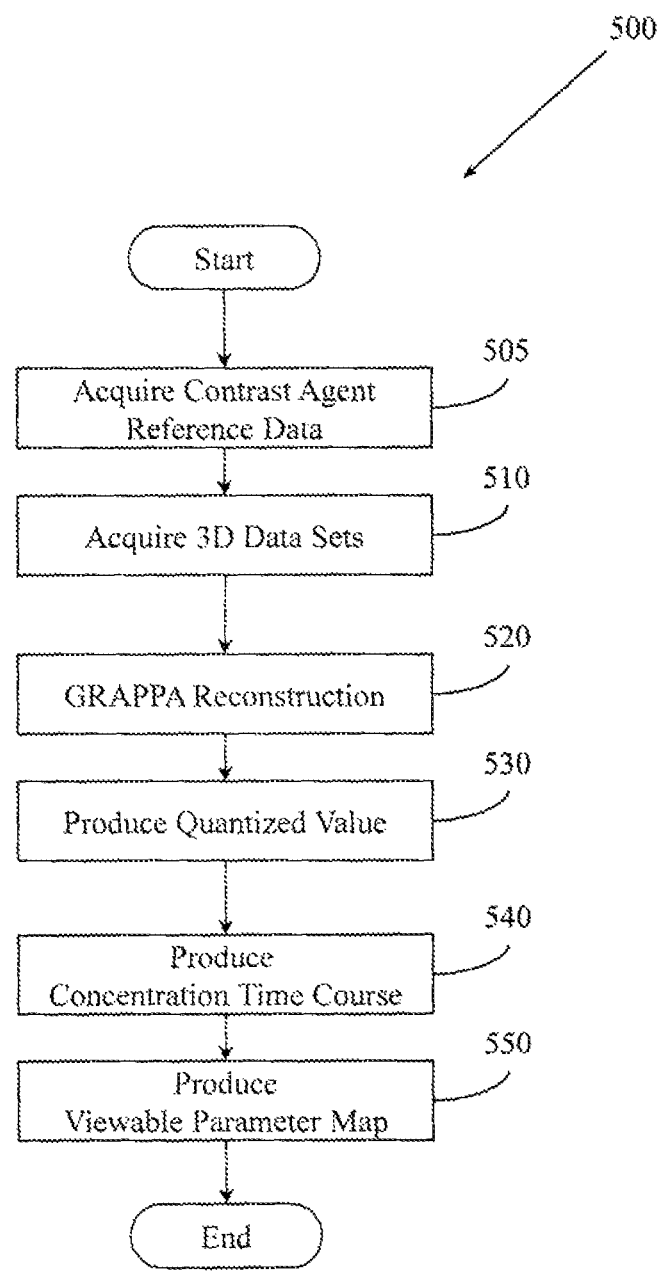
FIG. 5 illustrates an example method associated with MRI-based quantitative kidney perfusion analysis.

FIG. 5 illustrates an example method 500 associated with MRI-based quantitative kidney perfusion analysis. FIG. 5 includes some actions similar to those described in connection with method 400 (FIG. 4). For example, method 500 includes acquiring 3D data sets at 510, performing GRAPPA reconstruction at 520, and producing a quantized value at 530. However, method 500 includes additional actions.

In one example, producing the quantized value for the renal perfusion parameter includes converting a signal intensity value in a member of the series of 3D data sets to a value describing the concentration of the contrast agent. Converting the signal intensity value to the value describing the concentration of the contrast agent may be based, at least in part, on a reference signal intensity value associated with a reference sample of the contrast agent. Thus, in one embodiment, method 500 may include, at 505, acquiring the reference signal from the reference sample during the acquisition of at least one of the 3D data sets. The reference sample may provide, for example, a known concentration(s) of the contrast agent at a known location(s). For example, a vial(s) having compartments with four different known concentrations of contrast agent may be placed on the patient whose kidney is being examined.

Method 500 also includes, at 540, controlling the MRI apparatus to produce a concentration time course from a set of values describing the concentration of the contrast agent. Members of the set of values may be produced from members of the series of 3D data sets. In one embodiment, the time course may include data points separated by less than three seconds. In one embodiment, the concentration time course may be associated with data acquired from the renal parenchyma. Other time courses may be created.

Method 500 may also include, at 550, producing and displaying a viewable parameter map of the renal perfusion parameter. In one embodiment, the viewable parameter map may display information concerning the renal cortex. Other viewable parameter maps may be produced. In one embodiment, producing the viewable parameter map includes performing pixel-wise parameter mapping to produce a pixel-wise parameter map. In one embodiment, the pixel-wise parameter may be segmented by thresh-holding signal intensity values in a frame during corticomedullary enhancement.

While FIGS. 4 and 5 illustrate various actions occurring in serial, it is to be appreciated that various actions illustrated in FIGS. 4 and 5 could occur substantially in parallel. By way of illustration, a first process could acquire NMR signals, a second process could reconstruct the NMR signals, and a third process could produce quantized perfusion values. While three processes are described, it is to be appreciated that a greater and/or lesser number of processes could be employed and that lightweight processes, regular processes, threads, and other approaches could be employed.

In one example, a method may be implemented as computer executable instructions. Thus, in one example, a computer-readable storage medium may store computer executable instructions that if executed by a machine (e.g., processor) cause the machine to perform a method (e.g., methods 400 or 500). While executable instructions associated with the above method are described as being stored on a computer-readable storage medium, it is to be appreciated that executable instructions associated with other example methods described herein may also be stored on a computer-readable storage medium.

Figure 6:
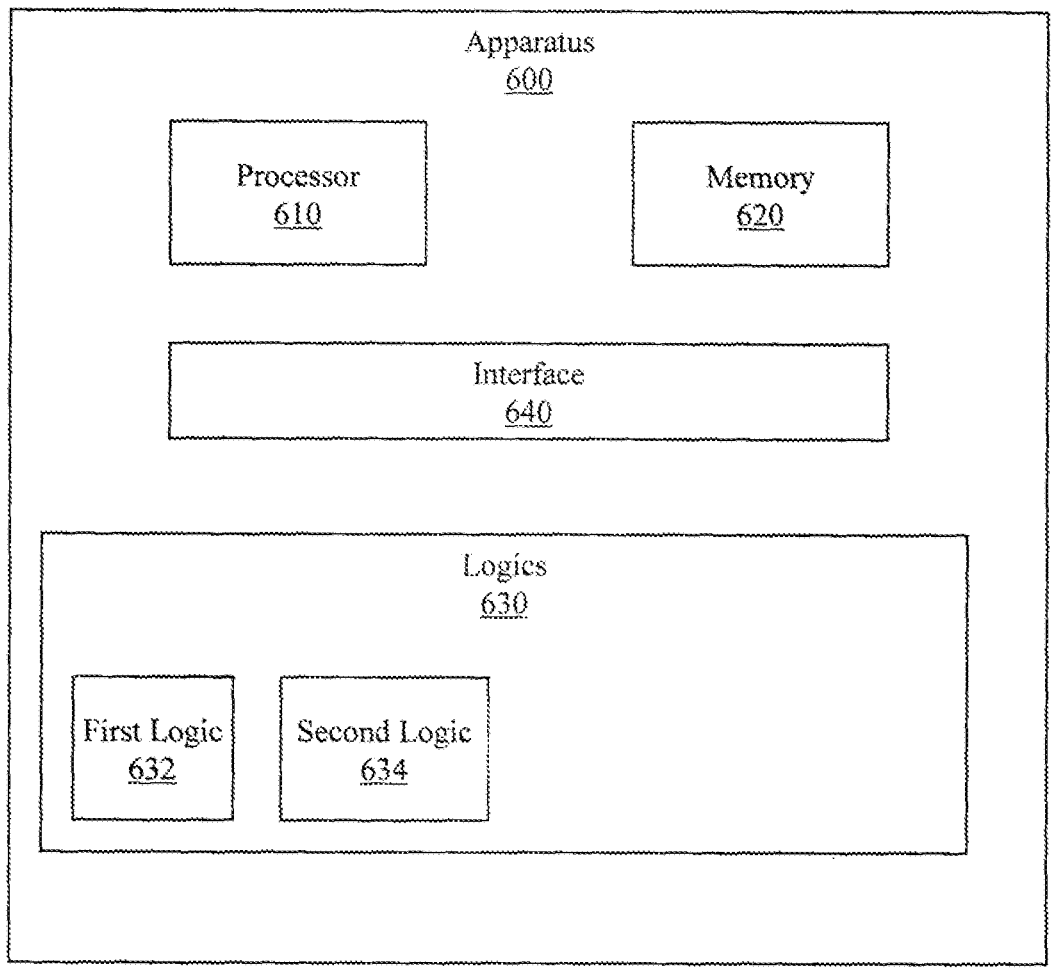
FIG. 6 illustrates an example apparatus associated with MRI-based quantitative kidney perfusion analysis.

FIG. 6 illustrates an apparatus 600 for performing MRI-based quantitative kidney perfusion analysis using a 3D through-time non-Cartesian GRAPPA approach for analyzing data acquired during a DCE MRI procedure. Apparatus 600 includes a processor 610, a memory 620, a set 630 of logics, and an interface 640 to connect the processor 610, the memory 620, and the set 630 of logics. In one embodiment, apparatus 600 may be a special purpose computer that is created as a result of programming a general purpose computer. In another embodiment, apparatus 600 may include special purpose circuits that are added to a general purpose computer to produce a special purpose computer.

In one embodiment, the set 630 of logics includes a first logic 632 and a second logic 634. In one embodiment, the first logic 632 is configured to reconstruct under-sampled 3D data associated with NMR signals acquired from a kidney experiencing NMR or by blood experiencing NMR. The blood experiencing NMR will be in or near the kidney experiencing NMR. In one embodiment, the under-sampled 3D data is associated with a DCE procedure that includes presenting a contrast agent (e.g., Gd-DTPA) to the kidney. The DCE procedure may produce various enhancements (e.g., corticomedullary, intra-renal, renal cortex, collecting system) in or near the kidney. In one embodiment, the first logic 632 reconstructs the data using a 3D through-time non-Cartesian GRAPPA approach.

In one embodiment, the second logic 634 is configured to produce a quantized value representing the concentration of a contrast agent in the kidney or blood. The quantized value may then be used to describe a perfusion parameter for the kidney or a filtration parameter for the kidney. The quantized value of the concentration may be based, at least in part, on a signal intensity in the under-sampled 3D data. The quantized value of the concentration may also be based, at least in part, on a two compartment model of the kidney. The two compartment model may include a plasma compartment and a tubular compartment. The quantized value may be precise to within fifty percent of the actual value represented by the quantized value.

In one embodiment, the second logic 634 may be configured to produce the quantized value for the contrast agent by converting a signal intensity value in the under-sampled 3D data to a value describing the concentration of the contrast agent. Converting the signal may be based, at least in part, on a reference signal intensity value associated with a reference sample of the contrast agent. The reference sample may be, for example, a vial having samples of contrast agent at various known concentrations positioned near the kidney. The reference signal intensity value may be acquired at least partially contemporaneously with the under-sampled 3D data.

While the second logic 634 is described as producing a quantized value, the second logic 634 may produce a plurality of quantized values that represent different concentrations at, different times. Additional processing and displays may be produced from the plurality of quantized values. For example, the second logic 634 may be configured to produce a concentration time course from a plurality of quantized values for the contrast agent. Producing the concentration time course facilitates performing and understanding functional analyses with a degree of precision that may not be possible with conventional systems. For example, temporal resolution of better than three seconds per frame may be achieved while also achieving renal parameter precision of greater than 50%, which provides data sufficient for high precision (e.g., clinically relevant) parameter mapping and display. 50% precision, or other precisions described herein, refer to how accurately the parameter reflects the actual condition in the kidney. For example, if a perfusion parameter actually has a value of 100 in the kidney, then 50% precision would be satisfied if the quantized value for the estimate of the perfusion parameter was within 50% of the actual value.

Figure 7:
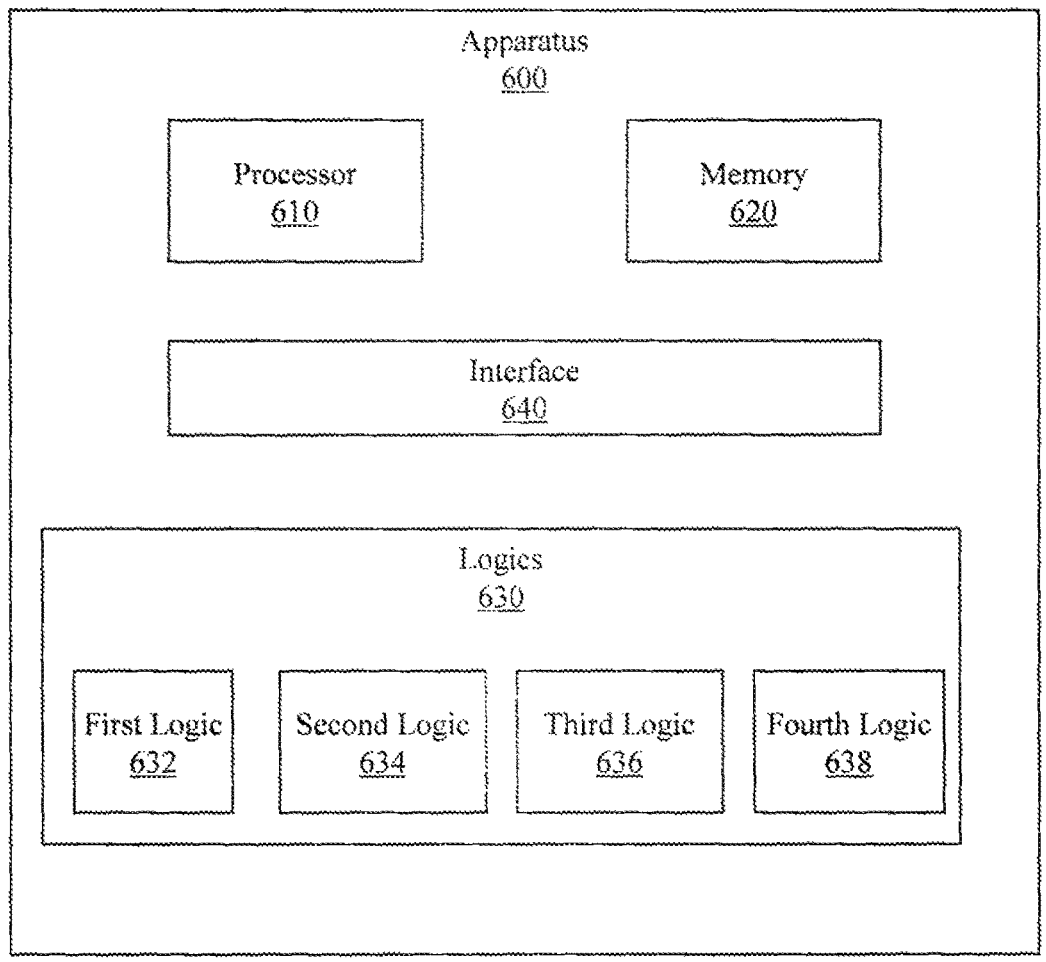
FIG. 7 illustrates an example apparatus associated with MRI-based quantitative kidney perfusion analysis.

FIG. 7 illustrates another embodiment of apparatus 600. This embodiment of apparatus 600 includes a third logic 636 that is configured to control an MRI apparatus to acquire the under-sampled three-dimensional data with a temporal resolution of better than 3 seconds per frame and with a spatial resolution of better than 2.85 mm$^3$. In one embodiment, third logic 636 may be user configurable with respect to temporal or spatial resolution. For example, a user may be able to select temporal resolution of 3 s/frame, 2.5 s/frame, 2.0 s/frame, or other resolutions and may be able to select spatial resolutions of 3.0 mm$^3$, 2.5 mm$^3$, 2.0 mm$^3$; or other resolutions.

This embodiment of apparatus 600 also includes a fourth logic 638 that is configured to produce and display a viewable parameter map associated with the quantized value or the concentration time course. Fourth logic 638 may produce the viewable parameter map by performing pixel-wise parameter mapping of a plurality of quantized values for the contrast agent. In one embodiment, the viewable parameter may be produced and displayed in real time as the DCE MRI procedure is in process.

Figure 8:
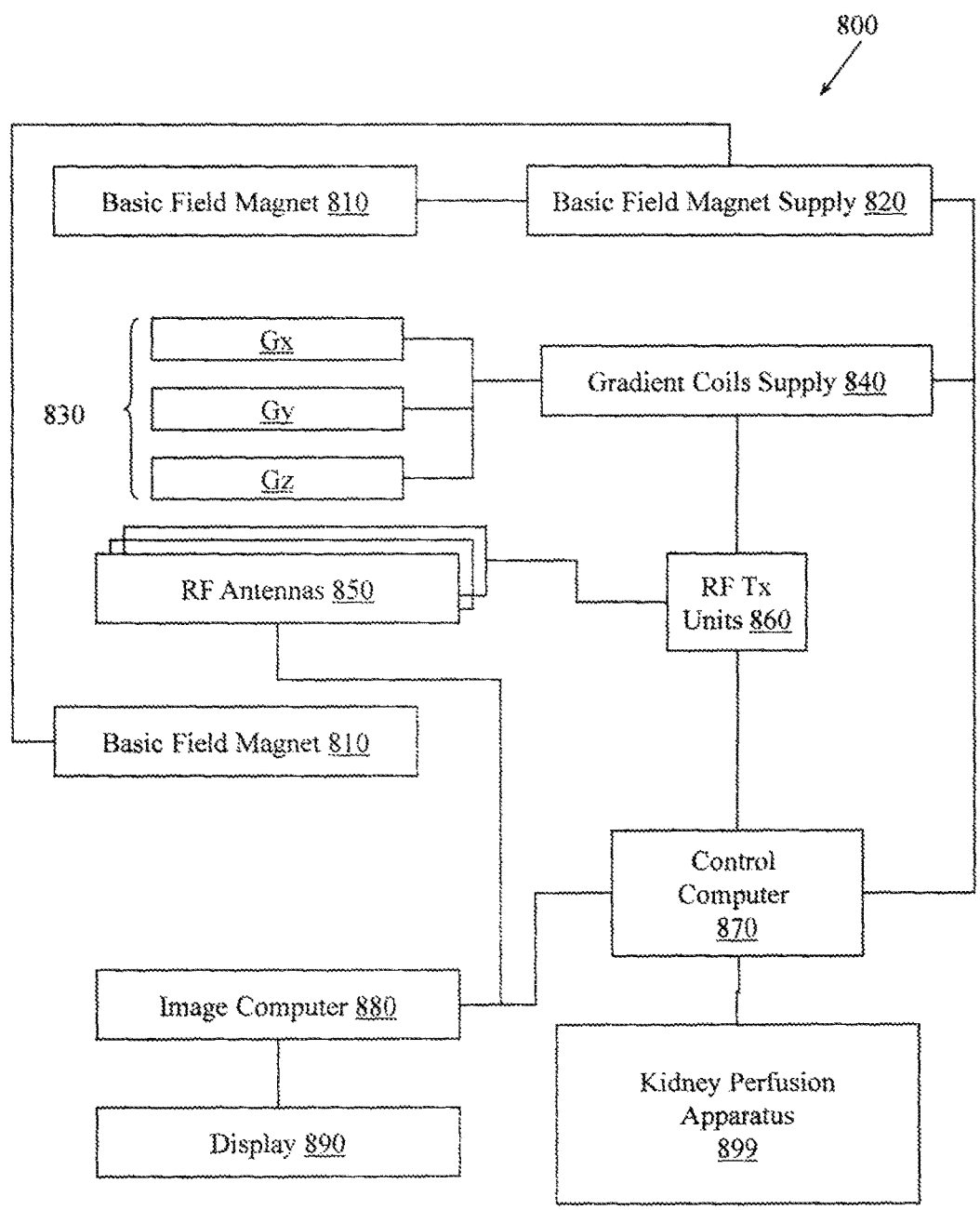
FIG. 8 illustrates an MRI apparatus configured to perform quantitative kidney perfusion analysis.

FIG. 8 illustrates an MRI apparatus 800. MRI apparatus 800 is configured with a kidney perfusion apparatus 899 to perform MRI-based quantitative kidney perfusion analysis. The kidney perfusion apparatus 899 may be configured with elements of example apparatus described herein or may perform example methods described herein.

The apparatus 800 includes a basic field magnet(s) 810 and a basic field magnet supply 820. Ideally, the basic field magnets 810 would produce a uniform $B_0$ field. However, in practice, the $B_0$ field may not be uniform, and may vary over an object being imaged by the MRI apparatus 800. MRI apparatus 800 may include gradient coils 830 configured to emit gradient magnetic fields like $G_S$, $G_P$ and $G_R$ or Gx, Gy, and Gz. The gradient coils 830 may be controlled, at least in part, by a gradient coils supply 840. In some examples, the timing, strength, and orientation of the gradient magnetic fields may be controlled, and thus selectively adapted, during an MRI procedure.

MRI apparatus 800 may include a set of RF antennas 850 that are configured to generate RF pulses and to receive resulting NMR signals from an object to which the RF pulses are directed. In one embodiment, the RF antennas 850 are arranged as an array of parallel transmission coils that are individually controllable. How the pulses are generated and how the resulting MR signals are received may be controlled and thus may be selectively adapted during an MR procedure. Separate RF transmission and reception coils can be employed. The RF antennas 850 may be controlled, at least in part, by a set of RF transmission units 860. An RF transmission unit 860 may provide a signal to an RF antenna 850. The RF transmission unit 860 may provide different signals to different RF antennas to produce different RF excitations from the different members of the array of parallel transmission coils. In one example, the different RF excitations may have different flip angles and different TRs.

The gradient coils supply 840 and the RF transmission units 860 may be controlled, at least in part, by a control computer 870. In one example, the control computer 870 may be programmed to control an NMR device as described herein. Conventionally, the magnetic resonance signals received from the RF antennas 850 can be employed to generate an image and thus may be subject to a transformation process like a two dimensional fast Fourier transform (FFT) that generates pixilated image data. The transformation can be performed by an image computer 880 or other similar processing device. The image data may then be shown on a display 890. While FIG. 8 illustrates an example MRI apparatus 800 that includes various components connected in various ways, it is to be appreciated that other MRI apparatus may include other components connected in other ways.

Some MRI applications desire both high resolution and high frame rates. Consider imaging a kidney that is affected by respiration or other motion. High resolution would facilitate improved diagnosis while high frame rates would facilitate improved motion artifact avoidance by acquiring an image while the kidney is at rest. High frame rates also facilitate functional analyses that show the kidney performing its functions. Motions other than respiration can also complicate kidney and other imaging. Therefore improvement in frame rates that do not sacrifice resolution, and improvements in resolution that do not sacrifice frame rates, are constantly being sought. One way to improve frame rates is to increase the degree of under-sampling.

Acquiring an MR image may include acquiring both calibration data and image data. Acquiring adequate calibration data facilitates under-sampling image data and yet still achieving acceptable resolution. However, in some cases, acquiring fully-sampled calibration data sets may consume as much or more time than acquiring data for an MR image. Thus, applications like acquiring a full 3D multi-phase data set of the kidney in a single breath hold may have been particularly challenging in conventional systems due, for example, to the time required to acquire fully-sampled data sets.

Conventionally, a single breath hold may only have allowed imaging a single slice of the kidney. When multiple slices were required, multiple breath holds were required. Multiple breath holds may be challenging for patients that are having their kidney imaged. Additionally, a patient may hold their breath differently on different breath hold attempts and thus images acquired during the different breath holds may be inconsistent. A further complication occurs as data is acquired further and further away from the time at which the calibration data was acquired. To mitigate these or other breath hold issues, example apparatus and methods facilitate performing kidney MRI with a free-breathing patient.

High resolution and high frame rates are also sought after in dynamic MRI. Dynamic MRI (dMRI) involves creating a sequence of MR images to monitor temporal changes in an object of interest (e.g., kidney perfusion). dMRI apparatus seek to acquire images as fast as possible while maintaining a sufficient signal-to-noise ratio (SNR) to investigate the object being imaged.

Conventional GRAPPA generates uncombined coil images for each coil in an array of receive coils used by a parallel magnetic resonance imaging (pMRI) apparatus. GRAPPA reconstructs missing lines in coil elements by forming linear combinations of neighboring lines to reconstruct individual missing data points. The weights for these linear combinations are derived by forming a fit between additionally acquired lines using a pseudo-inverse operation. GRAPPA is described in Griswold, et al., Proceedings of the ISMRM, Vol. 7, Issue 6, Pg. 1202-1210 (2002).

Conventional non-Cartesian GRAPPA acquires data and makes a reconstruction kernel comprised of GRAPPA weights. The reconstruction kernel is used to reconstruct acquisition path elements acquired during a radial reconstruction. The quality of a non-Cartesian GRAPPA reconstruction depends, at least in part, on whether a suitable reconstruction kernel that corresponds to an acquisition path element being reconstructed is available. Radial GRAPPA is described in Griswold et al., Proc. ISMRM 11, 2003, p 2349. While the radial trajectory provides a useful test bed for non-Cartesian trajectories, other non-Cartesian trajectories are possible. Non-Cartesian GRAPPA can include acquisition paths that include, for example, spiral acquisitions, rosette acquisitions, and other acquisitions.

Through-time GRAPPA facilitates achieving high frame rates and high resolution in applications like functional imaging of the kidney. Through-time non-Cartesian GRAPPA is described in US Patent Application 2011/0089946, now U.S. Pat. No. 8,542,012, filed Jan. 26, 2010 titled "Through-time Non-Cartesian GRAPPA Calibration". GRAPPA reconstruction depends on having useful GRAPPA weights to support the reconstruction. Computing a useful set of GRAPPA weights requires a threshold amount of differentiated calibration data. Differentiated calibration data is acquired from unique calibration frames. By applying a gradient in a direction perpendicular to a non-Cartesian encoded plane during acquisition of a fully-sampled calibration data scan, the data from the different applications of the perpendicular gradient or different partitions in the fully-sampled calibration data scan can be treated as unique calibration frames if at least three differences are produced in consecutive TRs. Therefore, fewer repetitions of the fully sampling calibration data scans are required to acquire the threshold amount of calibration data for computing GRAPPA weights. In one embodiment, consistently changing the perpendicular gradient in a known and controlled manner facilitates acquiring groups of lines having similar or identical gradients. While "lines" are described, one skilled in the art will appreciate that other acquisition elements (e.g., rays, spirals) may be similarly acquired.

Example apparatus and methods may acquire calibration data at different points in time (e.g., through time) and then perform a through-time GRAPPA calibration using the calibration data acquired at the different points in time. Useful calibration data can be derived from different groups of lines when the groups can be treated as separate time frames for the through-time calibration. The utility of the calibration data also depends on the calibration data being incoherent with image data acquired from a portion of an object that is moving. If the calibration data is acquired under similar conditions at different times, then the calibration data may be synchronized with the portion of the moving object rather than being incoherent with the portion of the moving object. When a calibration dataset (e.g., stack-of-stars) is phase encoded in a direction perpendicular to the non-Cartesian encoded plane, different groups experience a different gradient in the direction perpendicular to the non-Cartesian scan plane. When the gradient is changed in an orthogonal direction through time, the effective appearance of different groups of lines is different. Since different groups of lines have different effective appearances, the different groups of lines can be used to calibrate for through-time GRAPPA.

In one example, an under-sampled stack-of-stars dataset may be acquired in a segmented fashion during a single breath hold or during free-breathing. The data set may be reconstructed using through-time GRAPPA. For the calibration, multiple groups of lines acquired over multiple repetitions may be used to calibrate the individual in-plane GRAPPA weights and the through plane data. This facilitates reducing the number of fully-sampled repetitions employed for the reconstruction.

In GRAPPA, a missing k-space data point in a single coil can be reconstructed by a combination of acquired data points from other coils. The conventional one dimensional (1D) GRAPPA reconstruction is described by:

$$S(k_y + m\Delta k_y) = \hat{G}_{y,m} \cdot S(k_y), m=1 \ldots (R-1)$$

The vector $S(k_y)$ contains the acquired signal associated with the k-space location $k_y$, the signal being received in $N_c$ coils. The vector $S(k_y)$ has the length $N_c$. The vector $S(k_y+m\Delta k_y)$, of length $N_c$, contains the reconstructed signals at location $k_y+m\Delta k_y$ in the $N_c$ coils.

The weighting matrix $\hat{G}_{y,m}$, with size $N_c \times N_c$, contains coil weighting factors. In conventional GRAPPA, a weighting matrix can be calculated if fully-sampled reference data are available such that $S(k_y)$ and $S(k_y+m\Delta k_y)$ are known for desired shifts m, by solving:

$$\hat{G}_{y,m} = S(k_y+m\Delta k_y) \cdot (S(k_y)^H S(k_y))^{-1} (S(k_y)^H)$$

However, this conventional GRAPPA approach required a complete set of reference data that satisfied the Nyquist criterion and, as described, above, acquiring multiple complete sets of reference data may be impractical in some applications. Therefore, techniques like two dimensional through time calibration were developed.

Two dimensional through time calibration used an incomplete reference data set to calculate reconstruction parameters based on fitting neighboring k-space lines. While analyzing the relationship between adjacent lines in a reference data set theoretically provided knowledge to do complete reconstruction in an under-sampled frame, there was also information available about other relationships between lines in the reference data set. Therefore, in one example that used all available information, second relationships were used to fill missing lines to facilitate computing reconstruction parameters. The computed reconstruction parameters were then applied to the raw data of an under-sampled individual frame to grow a reference data set by filling in missing lines and finally to obtain a final data set. While a complete data set is described, it is to be appreciated that a less than complete data set may be created by iteratively applying information gathered from relationships between lines in the under-sampled data space. Additionally, when parallel processing was available, a reference data set may be grown in parallel.

GRAPPA reconstruction typically required a complete set of reference data for a shift in direction. By contrast, only one set of weights (reconstruction parameters) were needed by the GRAPPA operator (Gopr) technique to reconstruct a missing line from an acquired line. Only the single set of weights was used because GRAPPA reconstruction was reformulated as a matrix operator that shifts data in k-space. Once a first shift amount was determined, another shift amount was determined by repeated applications of the first shift amount. Thus, if a conversion was known for two neighboring (e.g., adjoining) lines, then a conversion for more distant lines could be determined from the known conversion. Thus, an entire (e.g., fully sampled) reference data set was not required.

Consider the following equation for determining a signal at a missing location $S_j(k_y+m\Delta k_y)$ based on an acquired signal:

$$S_j(k_y + m\Delta k_y) = \sum_{l=1}^{L} n(j, b, l, m) S_l(k_y + bA\Delta k_y)$$

$S_j(k_y)$ contains individual coil signals, n(j, b, l, m) represents reconstruction weights. The acquired signal at some position k in k-space in a coil j of the array is given by S(j,k). k is a vector that specifies the multi-dimensional location in k-space ($k_x$, $k_y$, $k_z$). For L coils, the 2D matrix is sized $L \times N_k$, where $N_k$ is the total number of k-space points in the image. Thus, the GRAPPA formulation could be converted to:

$$S_{(j,k+\Delta k)} = G_1 S_{(j,k)}$$

where the set of weights $G_1$ corresponds to n(j,b,l,m) for b=1, m=1, so that the individual rows of the $L \times LG$ matrix are the GRAPPA weights used to reconstruct the shifted line $S_{(j,k+\Delta k)}$ in each respective coil.

These calculations were used to describe an infinitesimal shift to derive a set of weights $G_d$ with a small shift of δ. The generalization was described according to:

$$S_{(j,k+\delta)} = G_\delta S_{(j,k)}$$

With this generalized shift described, other shifts could then be made through multiple applications of the weights matrix $G_\delta$. Thus, the GRAPPA fit process could be manipulated to produce an operator for shifting data in k-space. For example, if $G_1$ shifts the signal by Δk, a shift by mΔk is achieved by applying $G_1$ m-times: $S_{(j,k+m\Delta k)} = (G_1)^m \cdot S_{(j,k)}$.

The Gopr approach was extended to 3D imaging with accelerations along the phase-encoding and the 3D-encoding direction. For 3D imaging, raw data from three individual under-sampled time frames was assembled to calculate a reference data set. Reconstruction parameters for a Gopr reconstruction were then computed from the reference data set.

Re-gridding has been employed in non-Cartesian GRAPPA. Non-Cartesian GRAPPA improves on conventional pMRI processing using non-Cartesian trajectories. An under-sampled non-Cartesian (e.g., radial) acquisition will not acquire every possible ray in a radial pattern. Assuming that 360 rays are available, one for each degree in a circle associated with a radial pattern, a fully-sampled data set would require a ray at multiple rotations (e.g., 0 degrees, 1 degree, 2 degrees). However, in an under-sampled radial acquisition, less than every ray would be acquired. For example, rays may be acquired at 0 degrees, 2 degrees, 4 degrees, and at other angles. Therefore there are rays missing at 1 degrees, 3 degrees, and at other angles. However, these missing rays can be filled in using conventional GRAPPA techniques. Similarly, an under-sampled spiral or other non-Cartesian acquisition will not acquire every possible "line".

Calibration data may be acquired according to a plan that acquires acquisition path elements that are in the same configuration as acquisition path elements that will be used in a reconstruction. When data is acquired through time (e.g., at 1 second intervals), the reconstruction kernel may be exact for the acquisition path elements that are acquired multiple times through time. By repeatedly acquiring calibration data for an acquisition path element at different points in time throughout a period of time, a point in k-space to be solved for using the reconstruction kernel can be successfully reconstructed based on the high quality calibration data. Consider a calibration data set that acquires a calibration spiral for 0 degrees rotation and for 5 degrees rotation at several points in time throughout the period of time. At each point in time there will be a spiral for zero degrees and a spiral for five degrees. While the calibration data set need not be fully-sampled, it will be configured to have the same configuration as the reconstruction kernel. This means that if a reconstruction will rely on spirals for 0 degrees, 5 degrees, 10 degrees, etc., then the calibration data set will acquire, through time, multiple copies of calibration data for the reconstruction kernel spirals. The reconstruction kernel constructed from these repeatedly acquired spirals can be very accurate. While spirals are described, one skilled in the art will appreciate that other non-Cartesian acquisition trajectories may be employed.

Performing a through-time GRAPPA calibration could also be referred to as calibrating the MRI with a set of calibration data acquired at different points over a period of time. An under-sampled data set can be reconstructed using selected weights associated with calibration data acquired at different points in time. For example, a reconstruction can use weights from an immediately preceding calibration data set, from an immediately following calibration data set, from a combination of the before and after calibration data sets, from all the calibration data sets, and from other combinations. A weight set for each missing point can be calibrated and applied separately.

Figure 9:
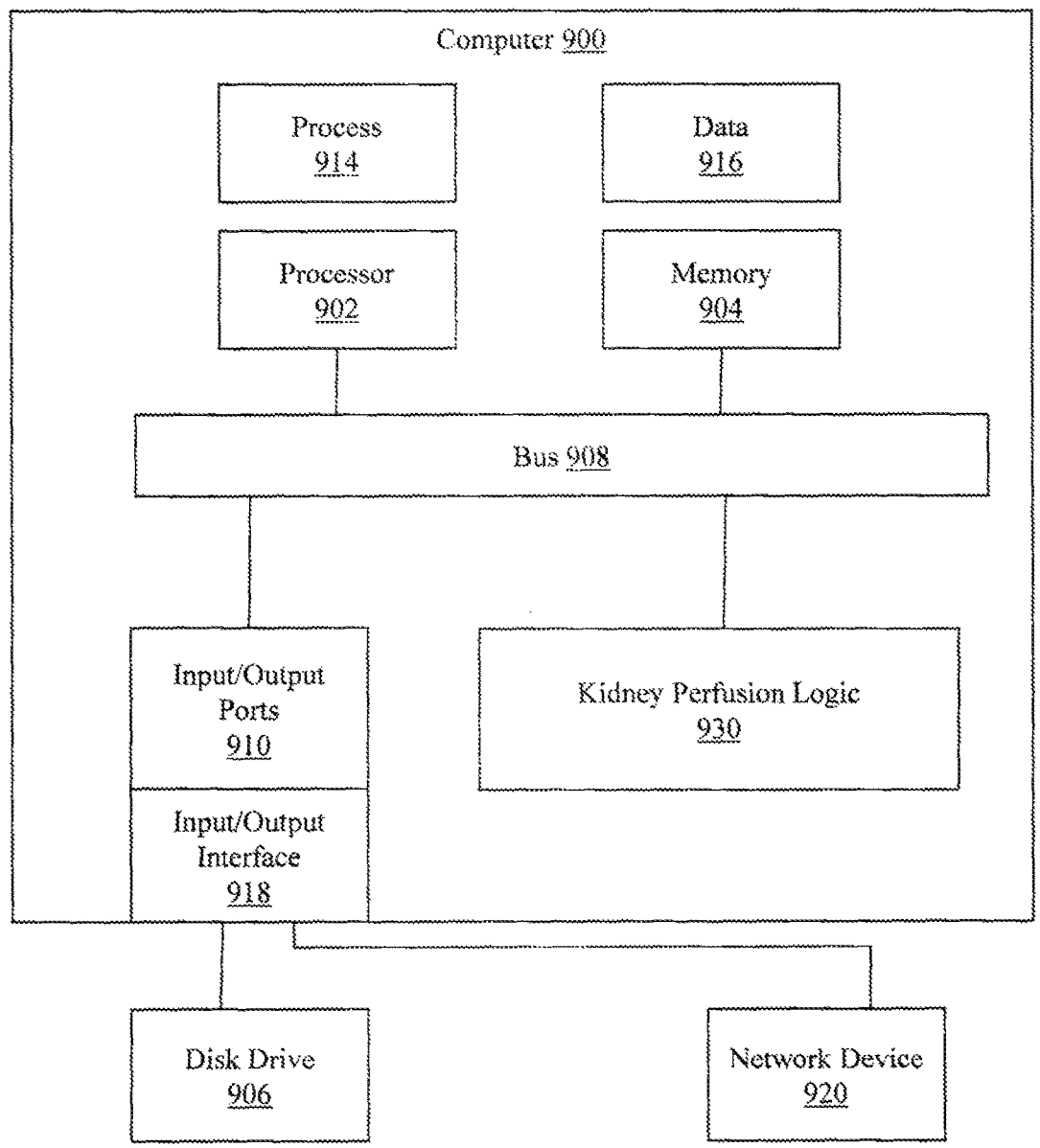
FIG. 9 illustrates a computer configured to perform MRI-based quantitative kidney perfusion analysis using a 3D through-time non-Cartesian GRAPPA approach.

FIG. 9 illustrates an example computing device in which example systems and methods described herein, and equivalents, may operate. The example computing device may be a computer 900 that includes a processor 902, a memory 904, and input/output ports 910 operably connected by a bus 908. In one example, the computer 900 may include a kidney perfusion logic 930 that facilitates performing MRI-based quantitative kidney perfusion analysis using a 3D non-Cartesian through-time GRAPPA approach in a DCE MRI.

In different examples, the logic 930 may be implemented in hardware, software, firmware, and/or combinations thereof. While the logic 930 is illustrated as a hardware component attached to the bus 908, it is to be appreciated that in one example, the logic 930 could be implemented in the processor 902.

Thus, logic 930 may provide means (e.g., hardware, software, firmware) for acquiring NMR signal data from the kidney according to a 3D through-time non-Cartesian generalized GRAPPA approach associated with a DCE procedure. Logic 930 may also provide means (e.g., hardware, software, firmware) for producing a quantized value of the concentration of the contrast agent in the kidney. In different embodiments the quantized value is accurate to within ten percent, twenty five percent, fifty percent, or a higher percent of the actual concentration of the contrast agent in the kidney. Logic 930 may also provide means for displaying an image that includes a representation of the quantized value. The means associated with logic 930 may be implemented, for example, as an application specific integrated circuit (ASIC). The means may also be implemented as computer executable instructions that are presented to computer 900 as data 916 that are temporarily stored in memory 904 and then executed by processor 902.

Generally describing an example configuration of the computer 900, the processor 902 may be a variety of various processors including dual microprocessor and other multi-processor architectures. A memory 904 may include volatile memory and/or non-volatile memory. Non-volatile memory may include, for example, read only memory (ROM), and programmable ROM (PROM). Volatile memory may include, for example, random access memory (RAM), static RAM (SRAM), and dynamic RAM (DRAM).

A disk 906 may be operably connected to the computer 900 via, for example, an input/output interface (e.g., card, device) 918 and an input/output port 910. The disk 906 may be, for example, a magnetic disk drive, a solid state disk drive, a floppy disk drive, a tape drive, a solid state drive (SSD), a flash memory card, or a memory stick. Furthermore, the disk 906 may be a CD-ROM drive, a CD-R drive, a CD-RW drive, a DVD ROM drive, a Blu-Ray drive, or an HD-DVD drive. The memory 904 can store a process 914 and/or a data 916, for example. The disk 906 and/or the memory 904 can store an operating system that controls and allocates resources of the computer 900.

The bus 908 may be a single internal bus interconnect architecture and/or other bus or mesh architectures. While a single bus is illustrated, it is to be appreciated that the computer 900 may communicate with various devices, logics, and peripherals using other busses (e.g., PCIE, 1394, USB, Ethernet). The bus 908 can be types including, for example, a memory bus, a memory controller, a peripheral bus, an external bus, a crossbar switch, and/or a local bus.

The computer 900 may interact with input/output (i/o) devices via the i/o interfaces 918 and the i/o ports 910. I/O devices may be, for example, a keyboard, a microphone, a pointing and selection device, cameras, video cards, displays, the disk 906, or the network devices 920. The input/output ports 910 may include, for example, serial ports, parallel ports, and USB ports.

The computer 900 can operate in a network environment and thus may be connected to the network devices 920 via the i/o interfaces 918, and/or the i/o ports 910. Through the network devices 920, the computer 900 may interact with a network. Through the network, the computer 900 may be logically connected to remote computers. Networks with which the computer 900 may interact include, but are not limited to, a LAN, a WAN, and other networks.

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the embodiments described herein. Therefore, the invention is not limited to the specific details, the representative apparatus, and illustrative examples shown and described. Thus, this application is intended to embrace alterations, modifications, and variations that fall within the scope of the appended claims.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and other similar exemplary language indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer component", as used herein, refers to a computer-related entity (e.g., hardware, firmware, software in execution, combinations thereof). Computer components may include, for example, a process running on a processor, a processor, an object, an executable, a thread of execution, and a computer. A computer component(s) may reside within a process and/or thread. A computer component may be localized on one computer and/or may be distributed between multiple computers.

"Computer communication", as used herein, refers to a communication between computing devices (e.g., computer, personal digital assistant, cellular telephone) and can be, for example, a network transfer, a file transfer, an applet transfer, an email, an HTTP transfer, and other transfer. A computer communication can occur across, for example, a wireless system (e.g., IEEE 802.11), an Ethernet system (e.g., IEEE 802.3), a token ring system (e.g., IEEE 802.5), a LAN, a WAN, a point-to-point system, a circuit switching system, a packet switching system, and other system.

"Computer-readable storage medium", as used herein, refers to a medium that stores instructions or data. "Computer-readable storage medium" does not refer to propagated signals, per se. A computer-readable storage medium may take forms, including, but not limited to, non-volatile media, and volatile media. Non-volatile media may include, for example, optical disks, magnetic disks, tapes, flash memory, ROM, and other media. Volatile media may include, for example, semiconductor memories, dynamic memory (e.g., dynamic random access memory (DRAM), synchronous dynamic random access memory (SDRAM), double data rate synchronous dynamic random-access memory (DDR SDRAM), etc.), and other media. Common forms of a computer-readable storage medium may include, but are not limited to, a floppy disk, a flexible disk, a hard disk, a magnetic tape, other magnetic medium, a compact disk (CD), other optical medium, a random access memory (RAM), a read only memory (ROM), a memory chip or card, a memory stick, and other media from which a computer, a processor or other electronic device can read.

"Data store", as used herein, refers to a physical and/or logical entity that can store data. A data store may be, for example, a database, a table, a file, a data structure (e.g. a list, a queue, a heap, a tree) a memory, a register, and other stores. In different examples, a data store may reside in one logical and/or physical entity and/or may be distributed between two or more logical and/or physical entities.

"Logic", as used herein, includes but is not limited to hardware, firmware, software in execution on a machine, and/or combinations of each to perform a function(s) or an action(s), and/or to cause a function or action from another logic, method, and/or system. Logic may include a software controlled microprocessor, a discrete logic (e.g., ASIC), an analog circuit, a digital circuit, a programmed logic device, a memory device containing instructions, and other entities. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

An "operable connection", or a connection by which entities are "operably connected", is one in which signals, physical communications, and/or logical communications may be sent and/or received. An operable connection may include a physical interface, an electrical interface, and/or a data interface. An operable connection may include differing combinations of interfaces and/or connections sufficient to allow operable control. For example, two entities can be operably connected to communicate signals to each other directly or through one or more intermediate entities (e.g., processor, operating system, logic, software). Logical and/or physical communication channels can be used to create an operable connection.

"Signal", as used herein, includes but is not limited to, electrical signals, optical signals, analog signals, digital signals, data, computer instructions, processor instructions, messages, a bit, a bit stream, and other items, that can be received, transmitted and/or detected.

"Software", as used herein, includes but is not limited to, one or more executable instructions that cause a computer, processor, or other electronic device to perform functions, actions and/or behave in a desired manner. "Software" does not refer to stored instructions being claimed as stored instructions per se (e.g., a program listing). The instructions may be embodied in various forms including routines, algorithms, modules, methods, threads, and/or programs including separate applications or code from dynamically linked libraries.

"User", as used herein, includes but is not limited to one or more persons, software, logics, computers or other devices, or combinations of these.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, ABC, AM, AAB, AABB, AABBC, AABBCC, (e.g., the data store may store only A, only B, only G, A&B, A&C, B&C, A&B&C, A&A&A, A&A&B, A&A&B&B, A&A&B&B&C, A&A&B&B&C&C). It is not intended to require one of A, one of B, and one of C. When the applicants intend to indicate "at least one of A, at least one of B, and at least one of C", then the phrasing "at least one of A, at least one of B, and at least one of C" will be employed.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

What is claimed is:

1. A non-transitory computer-readable storage medium storing computer executable instructions that when executed by a computer control the computer to perform a method, comprising:

controlling a magnetic resonance imaging (MRI) apparatus to acquire a series of three-dimensional (3D) data sets with a temporal resolution of better than 3 seconds per frame or with a spatial resolution of better than 2.85 mm$^3$, where a member of the series of 3D data sets is associated with a portion of a kidney, and where the series of 3D data sets are acquired during a free-breathing dynamic contrast enhanced (DCE) MRI procedure that includes presenting a contrast agent to the kidney;

controlling the MRI apparatus to reconstruct the series of 3D data sets into a corresponding series of 3D images using a 3D through-time non-Cartesian generalized auto-calibrating partially parallel acquisitions (GRAPPA) approach;

registering members of the series of 3D images to account for motion during the free-breathing DCE MRI procedure;

producing a quantified value for a renal perfusion parameter for the kidney as a function of a signal intensity associated with the concentration of contrast agent in the kidney as displayed in one or more members of the series of 3D images and as a function of a two compartment model of a kidney, where the two compartment model includes a plasma compartment and a tubular compartment, where producing the quantified value for the renal perfusion parameter includes converting a signal intensity value in a member of the series of 3D data sets to a value describing the concentration of the contrast agent; and producing and displaying a viewable parameter map of the renal perfusion parameter, where producing the viewable parameter map comprises performing pixel-wise parameter mapping to produce a pixel-wise parameter map, where the viewable parameter map displays information concerning the renal cortex.

2. The non-transitory computer-readable storage medium of claim 1, where the renal perfusion parameter is perfusion.

3. The non-transitory computer-readable storage medium of claim 1, where the renal perfusion parameter is mean transit time in the plasma compartment or mean transit time in the tubular compartment.

4. The non-transitory computer-readable storage medium of claim 1, where the renal perfusion parameter tubular flow.

5. The non-transitory computer-readable storage medium of claim 1, where the contrast agent is Gd-DTPA.

6. The non-transitory computer-readable storage medium of claim 1, where the DCE MRI procedure produces a corticomedullary enhancement in the kidney, an intra-renal enhancement in the kidney, a renal cortex enhancement in the kidney, or an enhancement in the collecting system of the kidney.

7. The non-transitory computer-readable storage medium of claim 1, the method comprising controlling the MRI apparatus to acquire the series of 3D data sets using a 3D stack-of-stars trajectory.

8. The non-transitory computer-readable storage medium of claim 1, the method comprising controlling the MRI apparatus to acquire the series of 3D data sets using radial under-sampling at a factor of at least eight.

9. The non-transitory computer-readable storage medium of claim 1, the method comprising controlling the MRI apparatus to acquire the series of 3D data sets using a bandwidth range of 580-820 Hz/pixel.

10. The non-transitory computer-readable storage medium of claim 1, the method comprising controlling the MRI apparatus to acquire the series of 3D data sets using a range of 20-24 projections per partition.

11. The non-transitory computer-readable storage medium of claim 1, the comprising controlling the MRI apparatus to acquire the series of 3D data sets using a partial Fourier transformation in the partition direction.

12. The non-transitory computer-readable storage medium of claim 1, where converting the signal intensity value to the value describing the concentration of the contrast agent is based, at least in part, on a reference signal intensity value associated with a reference sample of the contrast agent, where a reference signal is acquired from the reference sample during the acquisition of at least one of the 3D data sets.

13. The non-transitory computer-readable storage medium of claim 1, the method comprising controlling the MRI apparatus to produce a concentration time course from a plurality of values describing the concentration of the contrast agent.

14. The non-transitory computer-readable storage medium of claim 13, where the concentration time course is associated with the renal parenchyma.

15. The non-transitory computer-readable storage medium of claim 1, the method comprising reconstructing the series of 3D data sets without performing view sharing.

16. The non-transitory computer-readable storage medium of claim 1, the method comprising segmenting the pixel-wise parameter map by threshholding signal intensity values in a frame during corticomedullary enhancement.

17. The non-transitory computer-readable storage medium of claim 1, the method comprising producing the quantified value for the renal perfusion parameter with at least 10% precision.

18. The non-transitory computer-readable storage medium of claim 1, the method comprising producing the quantified value for the renal perfusion parameter with at least 25% precision.

19. The non-transitory computer-readable storage medium of claim 1, the method comprising producing the quantified value for the renal perfusion parameter with at least 50% precision.

20. The non-transitory computer-readable storage medium of claim 1, the method comprising producing the quantified value for the renal perfusion parameter with at least 75% precision.

21. An apparatus, comprising:
a memory having stored thereon under-sampled three-dimensional (3D) data associated with nuclear magnetic resonance (NMR) signals acquired from a kidney experiencing NMR or from blood in the kidney experiencing NMR;
a processor configured to access the memory and to:
reconstruct the data into images using a 3D through-time non-Cartesian generalized auto-calibrating partially parallel acquisitions (GRAPPA) approach, and
produce a quantized value for a contrast agent concentration in the kidney or blood in the kidney from a signal intensity in the under-sampled 3D data associated with the images based, at least in part, on a two compartment model of the kidney, where the two compartment model includes a plasma compartment and a tubular compartment, where the quantized value describes a perfusion parameter for the kidney or a filtration parameter for the kidney, and based, at least in part, on a reference signal intensity value associated with a reference sample of a contrast agent, where the reference signal intensity value is acquired at least partially contemporaneously with the under-sampled 3D data.

22. The apparatus of claim 21, where the quantized value describes perfusion in the kidney, mean transit time in the plasma compartment, tubular flow in the kidney, or mean transit time in the tubular compartment.

23. The apparatus of claim 21, where the under-sampled 3D data is associated with a free-breathing dynamic contrast enhanced (DCE) procedure that includes presenting the contrast agent to the kidney, where the contrast agent is Gd-DTPA.

24. The apparatus of claim 23, where the DCE procedure produces a corticomedullary enhancement in the kidney, an intra-renal enhancement in the kidney, a renal cortex enhancement in the kidney, or an enhancement in the collecting system of the kidney.

25. The apparatus of claim 24, where the under-sampled 3D data is under-sampled in a partition by a factor of at least four.

26. The apparatus of claim 25, wherein the processor is further configured to control an MRI apparatus to acquire the under-sampled three-dimensional data with a temporal resolution of better than 3 seconds per frame and with a spatial resolution of better than 3.0 mm$^3$.

27. The apparatus of claim 21, where the under-sampled 3D data includes at least fifty data sets associated with at least fifty different points in time at which the kidney is imaged, and where the processor is configured to produce a concentration time course from a plurality of quantized values for the contrast agent.

28. The apparatus of claim 27, wherein the processor is further configured to produce and display a viewable perfusion parameter map by performing pixel-wise parameter mapping of the plurality of quantized values for the contrast agent.

* * * * *